US010029958B2

(12) United States Patent
Dreux et al.

(10) Patent No.: US 10,029,958 B2
(45) Date of Patent: Jul. 24, 2018

(54) METHOD FOR THE PRODUCTION OF PARAXYLENE, COMPRISING TWO SIMULATED MOVING BED SEPARATION AND TWO ISOMERIZATION UNITS, ONE BEING IN THE GAS PHASE

(71) Applicant: IFP Energies nouvelles, Rueil-Malmaison (FR)

(72) Inventors: Heloise Dreux, Lyons (FR); Philibert Leflaive, Mions (FR); Damien Leinekugel Le Cocq, Oullins (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 9 days.

(21) Appl. No.: 15/326,887

(22) PCT Filed: Jun. 10, 2015

(86) PCT No.: PCT/EP2015/062984
§ 371 (c)(1),
(2) Date: Jan. 17, 2017

(87) PCT Pub. No.: WO2016/008653
PCT Pub. Date: Jan. 21, 2016

(65) Prior Publication Data
US 2017/0210683 A1 Jul. 27, 2017

(30) Foreign Application Priority Data
Jul. 18, 2014 (FR) ...................................... 14 56941

(51) Int. Cl.
*C07C 5/27* (2006.01)

(52) U.S. Cl.
CPC .......... *C07C 5/2737* (2013.01); *C07C 5/2775* (2013.01); *C07C 2529/40* (2013.01); *C07C 2529/74* (2013.01)

(58) Field of Classification Search
CPC . C07C 5/2737; C07C 5/2775; C07C 2529/40; C07C 2529/74
See application file for complete search history.

(56) References Cited

U.S. PATENT DOCUMENTS

| 7,915,471 | B2 | 3/2011 | Leflaive et al. |
| 2007/0249882 | A1* | 10/2007 | Ou ........................ C07C 5/2729 585/478 |
| 2008/0262282 | A1 | 10/2008 | Leflaive et al. |
| 2014/0155667 | A1 | 6/2014 | Ou et al. |

FOREIGN PATENT DOCUMENTS

FR 2862638 A1 5/2005

OTHER PUBLICATIONS

International Search Report for PCT/EP2015/062984 dated Aug. 12, 2015.

* cited by examiner

*Primary Examiner* — Brian A McCaig
*Assistant Examiner* — Jason Y Chong
(74) *Attorney, Agent, or Firm* — Millen, White, Zelano and Branigan, P.C.

(57) ABSTRACT

The present invention describes a process for the production of high-purity paraxylene from a xylenes cut containing xylenes and ethylbenzene, a process using two simulated moving bed separation units and two isomerization units.

20 Claims, 3 Drawing Sheets

METHOD FOR THE PRODUCTION OF PARAXYLENE, COMPRISING TWO SIMULATED MOVING BED SEPARATION AND TWO ISOMERIZATION UNITS, ONE BEING IN THE GAS PHASE

FIELD OF THE INVENTION

Paraxylene production has increased constantly for thirty years. Paraxylene is used mainly for the production of terephthalic acid and polyethylene terephthalate resins, in order to provide synthetic textiles, bottles, and plastic materials more generally.

In order to satisfy the ever-increasing demand for paraxylene, petrochemists have a choice between increasing the capacity of existing units or constructing new units.

The present invention makes it possible to respond to these two hypothetical cases. In particular it makes it possible to tackle increases in the capacity of existing units (called debottlenecking) as the modifications involved are relatively small.

In the remainder of the text reference will be made to the simulated moving bed separation unit (abbreviation SMB) or separation unit (SMB). A separation unit (SMB) may contain one or more adsorbers.

EXAMINATION OF THE PRIOR ART

The production of high-purity paraxylene by separation by adsorption is well known from the prior art. Industrially, this operation is carried out within a sequence of processes called "C8 aromatic loop". This "C8 aromatic loop" includes a stage of elimination of the heavy compounds (i.e. C9+) in a distillation column called "xylenes column". The top flow of this column, which contains the C8-aromatic isomers, is then sent to the process for the separation of the paraxylene, which is very generally a process of separation by adsorption in a simulated moving bed.

The extract, which contains the paraxylene is then distilled in an extraction column, then a so-called "toluene" column, in order to obtain high-purity paraxylene.

The raffinate, rich in metaxylene, orthoxylene and ethylbenzene, after a stage of elimination of the solvent by distillation, is treated in a catalytic isomerization unit which returns a mixture of C8 aromatics, in which the proportion of xylenes (ortho-, meta-, para-xylenes) is practically at thermodynamic equilibrium, and the quantity of ethylbenzene reduced. This mixture is again sent to the "xylenes column" with the fresh feedstock.

All the industrial processes for the isomerization of the C8-aromatics make it possible to isomerize the xylenes. On the other hand, the conversion of the ethylbenzene depends on the type of process and catalyst selected. In fact the petrochemical complexes will use a so-called "isomerizing" (i.e. isomerizing ethylbenzene to a mixture of C8-aromatics) or "dealkylating" (dealkylation of ethylbenzene to benzene) isomerization unit, in order to favour the production either of para-xylene alone, or of benzene and para-xylene respectively.

The choice of catalyst used depends on the desired conversion of the ethylbenzene. When the target reaction is the isomerization of the ethylbenzene, it requires a bi-functional catalyst having both an acid function and a hydrogenating function. It has in fact been demonstrated that the ethylbenzene is first hydrogenated to ethylcyclohexane on the metallic sites, then converted to dimethylcyclohexene on acid sites by contraction then expansion of the ring, and finally dehydrogenated to xylenes.

When the target reaction is the dealkylation of the ethylbenzene, it is produced only on the acid sites. However, the presence of a hydrogenating phase on the catalyst makes it possible to immediately hydrogenate the ethylene formed and to obtain complete dealkylation, thus avoiding any subsequent realkylation. In both cases, the incorporation of a metallic phase in the catalyst also makes it possible to ensure the stability thereof.

The industrial isomerization processes therefore use bifunctional heterogeneous catalysts (acid and metallic) utilized in a fixed bed and operating in vapour phase under hydrogen pressure, in temperature ranges generally comprised between 380-440° C. and pressures from 10 to 20 bar.

The choice of an "isomerizing" isomerization makes it possible, as indicated above, to maximize the production of paraxylene, which is the compound having the highest added value at the aromatic complex outlet. This solution however has the drawback of generating, during the isomerization stage, losses of aromatic rings by cracking that are greater than with a dealkylating isomerization, the ring being temporarily at least partially hydrogenated.

The choice of the type of isomerization is therefore a compromise between the minimization of the loss of aromatic rings associated with a coproduction of benzene, a product with a lower added value than paraxylene (dealkylating isomerization), and a maximization of the paraxylene production which has the drawback of generating greater losses of aromatic rings ("isomerizing" isomerization).

There is therefore a need for a process allowing both a maximization of the quantity of paraxylene produced and a reduced loss of aromatic rings.

Several solutions are proposed in the prior art for achieving this objective; these generally implement an isomerization (generally preferably dealkylating), combined with stages for the conversion of benzene by transalkylation and/or methylation of toluene or of benzene, as described for example in document US2013/0267746.

It has surprisingly been discovered that the combination, within an aromatic complex, of an "isomerizing" isomerization and a liquid-phase isomerization as described for example in patents US2011/263918, U.S. Pat. No. 7,371,913, U.S. Pat. No. 4,962,258 and U.S. Pat. No. 6,180,550 made it possible to maximize the quantity of paraxylene produced while having a reduced loss of aromatic rings with respect to an aromatic complex according to the prior art.

In the remainder of the text, by separation unit is meant simulated moving bed separation units; by adsorbers is meant assemblies of beds of adsorbent, a unit being capable of containing one or more adsorbers.

By isomerization unit and distillation columns is meant the other items of equipment of the process.

BRIEF DESCRIPTION OF THE INVENTION

Figure 1:
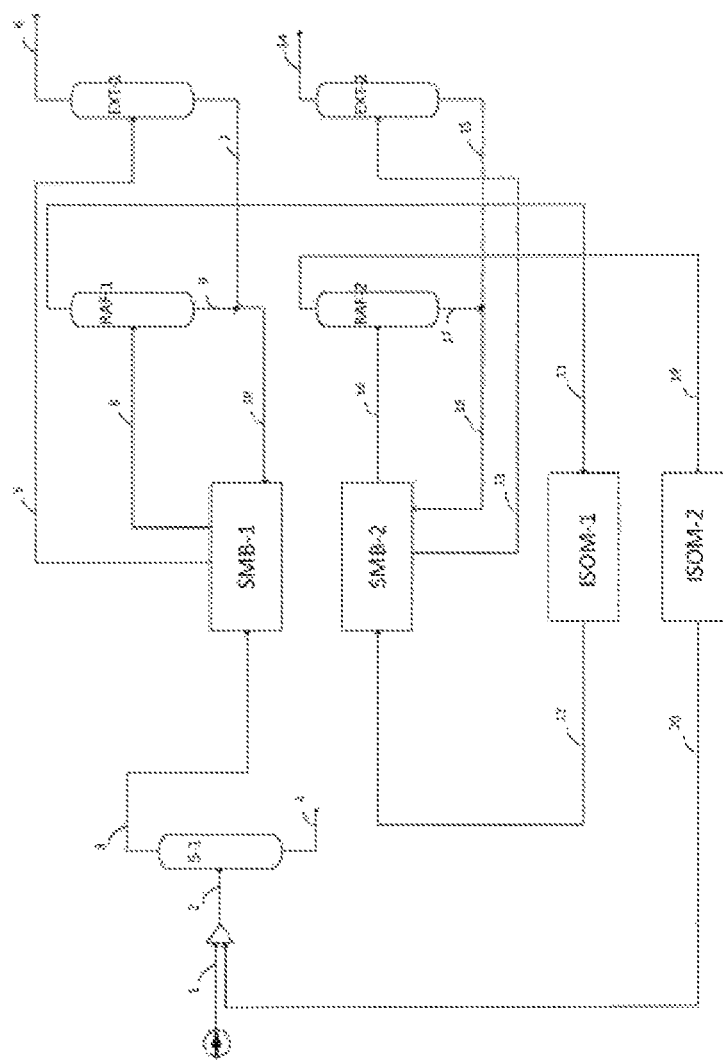
FIG. 1 is a layout of the process according to the present invention showing the two moving bed separation units denoted (SMB-1) and (SMB-2) and the two isomerization units denoted (ISOM-1) and (ISOM-2).

The present invention can be defined as a process for the production of high-purity paraxylene based on a xylenes cut containing ethylbenzene and C9+ compounds.

The process according to the present invention uses two moving bed separation units (SMB-1 and SMB-2) and two isomerization units (ISOM-1 and ISOM-2). Said process consists of the following series of stages:
- the feedstock (2) is sent to a distillation column (S-1) from which a mixture (3) is drawn off at the top comprising the major part of the metaxylene, paraxylene, ethylbenzene, and at least a part of the orthoxylene, and a flow (4) of C9-C10 hydrocarbons and the remaining part of the orthoxylene is drawn off at the bottom.
- a first separation of the mixture from the top (3) is carried out in the separation unit (SMB-1) comprising at least one adsorber containing a plurality of interconnected beds and operating in a closed loop, said unit comprising at least four zones delimited by the injections of the flow (3) and of the desorbent (10), resulting from the mixture of the flows (9) and (7), and the draw-offs of a first extract (5) enriched with paraxylene, and of a first raffinate (8) depleted of paraxylene,
- a second separation of the isomerate (12) originating from the isomerization unit (ISOM-1) is carried out in the separation unit (SMB-2), said separation unit (SMB-2) being constituted by at least one adsorber containing a plurality of interconnected beds and operating preferentially in a closed loop, and said unit comprising at least four zones delimited by the injections of the feedstock (12) and of the desorbent (18) resulting from the flows (17) and (15), and the draw-offs of a second extract (13) enriched with paraxylene, and of a second raffinate (16) depleted of paraxylene,
- the first extract (5) originating from the separation unit (SMB-1) is distilled in a distillation column (EXT-1), in order to recover a flow (6) enriched with paraxylene, and a flow (7) which is used as desorbent of the separation unit (SMB-1),
- the second extract (13) originating from the separation unit (SMB-2) is distilled in a distillation column (EXT-2), in order to recover a flow (14) enriched with paraxylene, and a flow (15) which is used as desorbent of the separation unit (SMB-2),
- the raffinate (16) originating from the separation unit (SMB-2) is distilled in a distillation column (RAF-2), so as to produce a flow (19) which supplies the isomerization unit (ISOM-2), and a flow (17) which is used as desorbent of the separation unit (SMB-2),
- the raffinate (8) originating from the separation unit (SMB-1) is distilled in a distillation column (RAF-1) which produces the flow (11) which supplies the isomerization unit (ISOM-1), and a flow (9) which is used as desorbent of the separation unit (SMB-1),
- the isomerization unit (ISOM-1) is supplied with the flow (11), in order to obtain the first isomerate (12),
- the second isomerization unit (ISOM-2) is supplied with the flow (19), in order to obtain a second isomerate (20), which is recycled to the inlet of the distillation column (S-1), said isomerization unit (ISOM-2) operating in gas phase and under the following conditions.
    - temperature greater than 300° C., preferably from 350° C. to 480° C.,
    - pressure less than 4.0 MPa and preferably from 0.5 to 2.0 MPa,
    - hourly space velocity less than 10 $h^{-1}$, preferably comprised between 0.5 $h^{-1}$ and 6 $h^{-1}$,
    - hydrogen to hydrocarbon molar ratio less than 10, and preferably comprised between 3 and 6.
    and the catalyst used in said isomerization unit ISOM-2 comprising at least one zeolite having channels the opening of which is defined by a ring with 10 to 12 oxygen atoms (denoted 10 MR or 12 MR), and at least one group VIII metal at a content comprised between 0.1 and 0.3% by weight, inclusive.

Preferably, in the process for the production of high-purity paraxylene according to the invention, the isomerization unit (ISOM1) operates in liquid phase under the following conditions:
- Temperature less than 300° C., preferably comprised between 200 and 260° C.,
- Pressure less than 4 MPa, preferably comprised between 2 and 3 MPa,
- Hourly space velocity less than 10 $h^{-1}$, preferably comprised between 2 $h^{-1}$ and 4 $h^{-1}$,
- Catalyst comprising at least one zeolite having channels the opening of which is defined by a ring with 10 or 12 oxygen atoms (denoted 10 MR or 12 MR), preferentially a catalyst a zeolite having channels the opening of which is defined by a ring with 10 oxygen atoms (denoted 10 MR), and even more preferably, a zeolite of the ZSM-5 type.

Preferably, in the process for the production of high-purity paraxylene according to the invention, the catalyst used for the gas-phase isomerization unit (ISOM-2) contains a zeolite of the EUO or MOR structure type and, preferably, an EU-1 zeolite and platinum.

According to a variant of the process for the production of high-purity paraxylene according to the invention, the separation unit (SMB-1) uses PDEB as desorbent.

According to another variant of the process for the production of high-purity paraxylene according to the invention, the separation unit (SMB-2) uses toluene as desorbent.

According to a variant of the process for the production of high-purity paraxylene according to the invention, the separation units (SMB1) and (SMB2) each contain from 6 to 24 beds, and preferably from 8 to 15 beds, distributed over one or more adsorbers, the number of beds being adjusted so that each bed preferably has a height comprised between 0.70 m and 1.40 m.

Preferably, in the process for the production of high-purity paraxylene according to the invention, the distribution of the quantity of solid adsorbent in the separation units (SMB-1) and (SMB-2) is as follows:
- the quantity of solid adsorbent in zone 1 is 17%±5%,
- the quantity of solid adsorbent in zone 2 is 42%±5%,
- the quantity of solid adsorbent in zone 3 is 25%±5%,
- the quantity of solid adsorbent in zone 4 is 17%±5%,
the zones being defined as follows:
- zone 1 being comprised between the injection of the desorbent and the draw-off of the extract,
- zone 2 being comprised between the draw-off of the extract and the injection of the feedstock,
- zone 3 being comprised between the injection of the feedstock and the draw-off of the raffinate,
- zone 4 being comprised between the draw-off of the raffinate and the injection of the desorbent.

According to another preferred variant of the process for the production of high-purity paraxylene according to the invention, as regards the separation unit (SMB-1), the ratio by volume of desorbent to feedstock is at least 1.7/1 and preferably comprised between 1.5/1 and 0.4/1, inclusive.

According to another variant of the process for the production of high-purity paraxylene according to the invention, as regards the separation unit (SMB-2), the ratio by volume of desorbent to feedstock is at least 1.7/1 and preferably comprised between 1.5/1 and 0.4/1, inclusive.

One of the advantages of the process for the production of high-purity paraxylene according to the invention, is that it makes it possible to debottleneck an existing separation unit, constituted by two adsorbers used in series, as follows:
- the last bed of the first adsorber is connected to the first bed of the first adsorber via a line containing at least one recirculation pump, this first adsorber acting as a separation unit (SMB-1)
- the last bed of the second adsorber is connected to the first bed of the second adsorber via a line containing at least one recirculation pump, this second adsorber acting as a separation unit (SMB-2)

In a variant of the process for the production of high-purity paraxylene according to the invention, the configuration of the two separation units (SMB-1) and (SMB-2) has a fixed number of beds in each of the chromatographic zones of each of the two separation units (SMB-1) et (SMB-2).

Finally, in another variant of the process for the production of high-purity paraxylene according to the invention, a fraction of the isomerate (12) is sent to the distillation column (S-1).

Detailed Description of the Invention

The present description is based on FIG. 1.

The feedstock (2) is sent to a distillation column (S-1) from where a mixture (3) the major part comprising metaxylene, paraxylene, ethylbenzene, and at least a part orthoxylene is drawn off at the top, and from where a flow (4) of C9-C10 hydrocarbons and the remaining part of the orthoxylene is drawn off at the bottom.

A first separation of the mixture from the top (3) is carried out in the separation unit (SMB-1) in at least one adsorber containing a plurality of interconnected beds and operating in a closed loop, said adsorber comprising at least four zones delimited by the injections of the flow (3) constituting the first feedstock of the column and the desorbent (10), and the draw-offs of an extract (5) containing paraxylene, and of a raffinate (8) containing orthoxylene and metaxylene.

The four zones correspond to the following definitions:
1)—zone 1 is comprised between the injection of the desorbent (10) and the draw-off of the extract (5),
2)—zone 2 is comprised between the draw-off of the extract (5) and the injection of the first adsorption feedstock (3),
3)—zone 3 is comprised between the injection of the first feedstock (3) and the draw-off of the raffinate (8) and,
4)—zone 4 is comprised between the draw-off of the raffinate (8) and the injection of the desorbent (10), Preferentially, a first extract (5) is distilled in a distillation column (EXT-1), in order to recover a first fraction (6) enriched with paraxylene, Preferentially, a first extract (8) is distilled in a distillation column (RAF-1), in order to eliminate substantially all the desorbent and in order to draw off a first distilled fraction (11). This first distilled fraction (11) supplies a first isomerization unit (ISOM-1) in order to obtain a first isomerate (12) preferentially supplying the xylenes separation unit (SMB-2), but capable of being partially recycled to the inlet of the distillation column (S-1).

A second separation of the isomerate (12) originating from the isomerization unit (ISOM-1) from which all or part of the heavy C9 and C10 compounds has been removed by distillation (either in a dedicated column, or in the column S-1), is carried out in the separation unit (SMB-2), the separation unit (SMB-2) being constituted by at least one adsorber containing a plurality of interconnected beds and operating preferentially in a closed loop, said column comprising at least four zones delimited by the injections of the flow (12) and of the desorbent (18), and the draw-offs of a second extract (13) containing paraxylene, and of a second raffinate (16).

The four zones are defined as follows:
1) zone 1 is comprised between the injection of the desorbent (18) and the draw-off of the extract (13),
2) zone 2 is comprised between the draw-off of the extract (13) and the injection of the second adsorption feedstock (12),
3) zone 3 is comprised between the injection of the feedstock (12) and the draw-off of the raffinate (16), and
4) zone 4 is comprised between the draw-off of the raffinate (16) and the injection of the desorbent (18), Preferentially, the second extract (13) is distilled in a distillation column (EXT-2), in order to recover a second fraction (14) enriched with paraxylene. The two extracts (5) and (13) can also be distilled in a single common extraction column in order to recover a single fraction enriched with paraxylene.

Preferentially, a second extract (16) is distilled in a distillation column (RAF-2), in order to eliminate substantially all the desorbent (17) and in order to draw off a second distilled fraction (19). This second distilled fraction (19) supplies a second isomerization unit (ISOM-2), in order to obtain a second isomerate (20), recycled to the inlet of the separation column (S-1).

The first isomerization unit (ISOM-1) operating preferably in liquid phase, is generally operated under the following conditions:
- Temperature less than 300° C., preferably 200° C. to 260° C.,
- Pressure less than 4 MPa, preferably 2 to 3 MPa,
- Hourly space velocity (HSV) less than 10 $h^{-1}$ (10 liters per liter per hour), preferably comprised between 2 and 4 $h^{-1}$,
- Catalyst comprising at least one zeolite having channels the opening of which is defined by a ring with 10 or 12 oxygen atoms (10 MR or 12 MR), preferentially a catalyst comprising at least one zeolite having channels the opening of which is defined by a ring with 10 oxygen atoms (10 MR), and even more preferably, a catalyst comprising a zeolite of ZSM-5 type.

The second isomerization unit (ISOM-2) is characterized in that the catalyst comprises at least one zeolite having channels the opening of which is defined by a ring with 10 or 12 oxygen atoms (10 MR or 12 MR), preferentially a catalyst comprising a zeolite of the EUO or MOR structure type, and at least one group VIII metal with a content comprised between 0.1 and 0.3% by weight inclusive, preferentially an EU-1 zeolite and platinum. This isomerization zone operating in gas phase, is generally operated under the following conditions:
- Temperature greater than 300° C., preferably 350° C. to 480° C., Pressure less than 4 MPa, preferably 0.5 to 2 MPa, Hourly space velocity (HSV) less than 10 h$^{-1}$ (10 liters per liter per hour), preferably comprised between 0.5 and 6 h$^{-1}$, H$_2$/hydrocarbons molar ratio less than 10, and preferably comprised between 3 and 6.

The desorbents used in the separation units (SMB-1 and SMB-2) are generally selected from paradiethylbenzene, toluene, paradifluorobenzene or diethylbenzenes in a mixture. The ratio by volume of the desorbent to the feedstock in the separation units (SMB-1 and SMB-2) is comprised between 0.5 and 2.5, and preferably comprised between 0.8 and 2.

The separation units (SMB-1 and SMB-2) are operated at a temperature comprised between ° C. and 250° C., preferably between 90° C. and 210° C., and even more preferably between 140° C. and 180° C., and under a pressure comprised between the bubble pressure of xylenes at the operating temperature and 2 MPa.

The operation of the process according to the invention, and in particular the composition of the different flows, is detailed hereinafter with reference to FIG. 1.

The fresh feedstock is introduced through the line (1) into a distillation column (S-1).

This fresh feedstock contains mainly C8-aromatic compounds, xylenes and ethylbenzene, in a variable proportion according to the origin of the cut. It can possibly contain impurities in a variable quantity depending on the origin of the feedstock which will be essentially C9 and C10 aromatic compounds and paraffinic and naphthenic compounds.

The content of naphthenic or paraffinic compounds is advantageously less than 1% by weight. Preferably, this content is less than 0.3% by weight, and even more preferably this content is less than 0.1% by weight.

The feedstock can originate either from a reforming unit, or from a toluene disproportionation unit, or from a unit for the transalkylation of toluene and C9 aromatics.

An isomerate conveyed by a line (20) is added to the fresh feedstock.

The bottom effluent (4) from the column (S-1) is essentially constituted by C9 and C10 aromatic compounds, and optionally orthoxylene. Optionally, the mixture (4) of orthoxylene and C9-C10 aromatic hydrocarbons drawn off at the bottom of the distillation column (S-1), can be sent into another distillation column from which a high-purity orthoxylene flow (at least 98.5%) is extracted at the top, and a flow containing C9-C10 hydrocarbons at the bottom.

The top effluent (3) from the column (S-1), constitutes the feedstock of the separation unit (SMB-1). The separation unit (SMB-1) is supplied on the one hand with the feedstock conveyed by the line (3), and on the other hand with the desorbent conveyed by a line (10).

The effluents from the separation unit (SMB-1) unit are an extract (5), a raffinate (8). The total number of beds of the separation unit (SMB-1) according to the invention is preferably comprised between 6 and 24 beds, and even more preferably between 8 and 15 beds distributed over one or more adsorbers.

The number of beds will be adjusted so that each bed preferably has a height comprised between 0.70 m and 1.40 m.

The distribution of the quantity of solid adsorbent in each zone is as follows:
the quantity of solid adsorbent in zone 1 is 17%±5%,
the quantity of solid adsorbent in zone 2 is 42%±5%,
the quantity of solid adsorbent in zone 3 is 25%±5%,
the quantity of solid adsorbent in zone 4 is 17%±5%, According to a preferred characteristic of the invention, it is possible to inject the desorbent and the feedstock into the separation unit in a ratio by volume of desorbent to feedstock of at most 1.7/1 and preferably comprised between 1.5/1 and 0.4/1, inclusive.

The extract (5) is essentially constituted by toluene, paraxylene and desorbent.

The raffinate (8) is essentially constituted by toluene, metaxylene and orthoxylene, ethylbenzene, paraxylene for the part not recovered in the extract, and desorbent.

The extract (5) is sent to a distillation column (EXT-1).

From the distillation column (EXT-1), the desorbent (7) which is sent back to the separation unit (SMB-1) through the line (10), and a flow enriched with paraxylene through the line (6) are drawn off.

The raffinate (8) is sent to a distillation column (RAF-1). From the distillation column (RAF-1), desorbent (9) which is sent back into the separation unit (SMB-1) through the line (10), and a mixture of metaxylene, orthoxylene and ethylbenzene which is sent to the isomerization unit (ISOM-1) through a line (11), are drawn off.

The isomerization unit (ISOM-1) preferentially in liquid phase, can operate under the following conditions:
temperature less than 300° C., preferably comprised between 200 and 260° C.,
pressure less than 4 MPa, preferably comprised between 2 and 3 MPa,
hourly space velocity less than 10 h$^{-1}$, preferably comprised between 2 h$^{-1}$ and 4 h$^{-1}$, All the catalysts capable of isomerizing hydrocarbons with 8 carbon atoms are suitable for the isomerization unit (ISOM-1) of the present invention. Preferably, a catalyst containing a zeolite of type ZSM-5 is used.

The effluent from the isomerization unit (ISOM-1) is sent back through the line (12), either to the distillation column (S-1), or directly to the inlet of the separation unit (SMB-2) in the case where the content of compounds other than the C8 aromatics is very low, typically of the order of 1% by weight. The C9 content is typically less than 1000 ppm by weight.

The effluents from the separation unit (SMB-2) unit are an extract (13), a raffinate (16).

The total number of beds of the separation unit (SMB-2) according to the invention is preferably comprised between 6 and 24 beds, and even more preferably comprised between 8 and 15 beds distributed over one or more adsorbers.

The number of beds will be adjusted so that each bed preferably has a height comprised between 0.70 m and 1.40 m.

The distribution of the quantity of solid adsorbent in each zone is preferentially as follows:
the quantity of solid adsorbent in zone 1 is 17%±5%,
the quantity of solid adsorbent in zone 2 is 42%±5%,
the quantity of solid adsorbent in zone 3 is 25%±5%,
the quantity of solid adsorbent in zone 4 is 17%±5%, According to a preferred characteristic of the invention, it is possible to inject the desorbent and the feedstock into the separation unit (SMB-2), in a ratio by volume of desorbent to feedstock of at most 1.7/1 and preferably comprised between 1.5/1 and 0.4/1, inclusive.

The configuration (average number of beds per zone) of the two separation units (SMB-1 and SMB-2) can be:
having a fixed number of beds in each of the chromatographic zones (mode known as "simulated moving bed" as defined in patent FR2 976 501), having a variable number of beds for one adsorber ("VARICOL" mode as defined in patent FR 2 976 501) and a fixed number for the other,
having a variable number of beds for both adsorbers.

The extract (13) is essentially constituted by toluene, paraxylene and desorbent.

The raffinate (16) is essentially constituted by toluene, metaxylene and orthoxylene, ethylbenzene, paraxylene with respect to the part not recovered in the extract, and desorbent. The extract (13) is sent into a distillation column (EXT-2).

From the distillation column (EXT-2), the desorbent (15) which is sent back into the separation unit (SMB-2) through the line (18), and a flow enriched with paraxylene through the line (14) are drawn off.

The raffinate is sent through a line (16) into the distillation column (RAF-2).

From the distillation column (RAF-2) the desorbent (17) which is reintroduced through the line (18) into the separation unit (SMB-2), and a mixture of xylenes and ethylbenzene through a line (19), are drawn off.

The effluents of the line (19) are sent to the isomerization unit (ISOM-2) operating at a high temperature in vapour phase.

The isomerization unit (ISOM-2) is preferably operated under the following conditions:
 temperature greater than 300° C., preferably from 360° C. to 480° C.,
 pressure less than 2.5 MPa and preferably comprised between 0.5 to 0.8 MPa,
 hourly space velocity less than 10 h$^{-1}$, preferably comprised between 0.5 h$^{-1}$ and 6 h$^{-1}$,
 hydrogen to hydrocarbon molar ratio less than 10, and preferably comprised between 3 and 6.

All the catalysts capable of isomerizing the hydrocarbons with 8 carbon atoms, zeolitic or not, are suitable for the isomerization unit (ISOM-2) of the present invention. Preferably, a catalyst containing an acid zeolite, for example of the MFI, MOR, MAZ, FAU and/or EUO structure type is used. Even more preferably, a catalyst is used containing a zeolite of the EUO structure type and at least one metal from group VIII of the periodic table.

Preferably, the catalyst of the isomerization unit (ISOM-2) contains from 1 to 70% by weight of a zeolite of the EUO structure type (EU-1 for example) comprising silicon and at least one element T preferably selected from aluminium and boron, the Si/T ratio of which is comprised between 5 and 100. Said zeolite is at least partially in the form of hydrogen, and the sodium content is such that the Na/T atomic ratio is less than 0.1. Optionally the catalyst of the isomerization unit can contain between 0.01 and 2% by weight of tin or indium, and sulphur at a content of 0.5 to 2 atoms per atom of the group VIII metal.

The effluent of the isomerization unit (ISOM-2) is sent into a separation system which makes it possible to recover a part of the hydrogen which is recycled to the isomerization unit (ISOM-2). The non-recycled part of the hydrogen is made up by an addition of fresh hydrogen. At the end of the separation system an isomerate constituted by the heaviest fractions is recovered, which is sent back to the distillation column (S-1) through the line (20).

The process according to the invention is particularly suitable for a modification to an existing unit for the purpose of increasing the quantity of paraxylene produced; an operation that is known as debottlenecking.

In the particular case of debottlenecking an existing aromatic loop, the invention consists of significantly increasing the flow rate of fresh feedstock and the flow rate of paraxylene produced, while continuing to use the main equipment of the loop, i.e.:
1) the xylenes distillation column (S-1)
2) the simulated moving bed xylenes separation unit, operating as 24 beds
3) the isomerization unit (ISOM-2) supplied with the raffinate drawn off from the separation column converting the ethylbenzene, said unit using for example a catalyst based on zeolite of the EUO structure type comprising a reactor, a recycling compressor, a stabilization column and a column allowing the C8 and C9 naphthenes to be recovered so as to recycle them to the feedstock,
4) the raffinate columns (RAF-1)
5) the extract column (EXT-1)

In order to carry out this debottlenecking according to the invention, a 24-bed simulated moving bed process containing two 12-bed adsorbers in series is converted to a process with two twelve-bed adsorbers, each connected in parallel. To this end:
 the twelfth bed of the first adsorber is connected to the first bed of said first adsorber via a line containing at least one recirculation pump,
 the twelfth bed of the second adsorber is connected to the first bed of said second adsorber via a line containing at least one recirculation pump.

The system controlling and regulating the injection flow rates of the feedstock and of the desorbent and the draw-off flow rates of the extract and of the raffinate of the 24-bed adsorption stage is adapted so as to be able to manage the injection and draw-off flow rates independently in each of the two adsorbers of the remodelled process according to the invention.

For the injection devices, this operation can be carried out either by doubling the pump+measurement device system in order to regulate the flow rate injected into each of the adsorbers, or, with the aim of minimizing costs, by using the pre-existing pump and measurement device which will manage the two flows to be injected as a whole, and by adding a system for the measurement and regulation of the flow rate supplying one of the two adsorbers.

When the supply or the draw-off of the fluids over all of the plates of the existing 24-bed process is ensured by a plurality of on-off controlled valves, there are no additional modifications to be made to the supply and draw-off networks.

When the supply or the draw-off of the fluids over all of the plates of the existing 24-bed process is ensured by the use of a multi-way rotary valve, these functions will preferably be ensured by the use of two multi-way rotary valves (optionally reusing the pre-existing valve on one of the two ways after adaptation).

In the case of an existing 24-bed unit constituted by twice twelve beds in series, the main flow circulates from the bottom of the first adsorber to the top of the second adsorber, and from the bottom of the second adsorber to the top of the first adsorber.

The flows originating from the bottoms of the two adsorbers are then redirected to circulate to the top of the adsorber from which they originated by carrying out modifications to the valves and pipes. The bottom flow from the first adsorber is recycled to the top of said adsorber and the bottom flow from the second adsorber is recycled to the top of said second adsorber.

The configuration (average number of beds per zone) of the two adsorbers can be carried out according to one of the 3 variants disclosed above, i.e.:

having a fixed number of beds in each of the chromatographic zones for the two absorbers,
having a variable number of beds for one adsorber and a fixed number for the other,
having a variable number of beds for both adsorbers.

In order to separate the second raffinate from the desorbent, a new distillation column (RAF-2) must also be installed. The flow of xylenes and ethylbenzene drawn off from the distillation column (RAF-2) will be isomerized in the vapour-phase isomerization unit (ISOM-1) as described above.

A second liquid-phase isomerization unit (ISOM-2) is added, the effluent from which will supply the separation unit (SMB-2) preferentially without passing through the distillation column (S-1) in order to avoid the addition of a second column for the separation of the xylenes.

Furthermore, an extract distillation column (EXT-2) must be added, supplied with the extract (13) from the separation unit (SMB-2).

Figure 2:
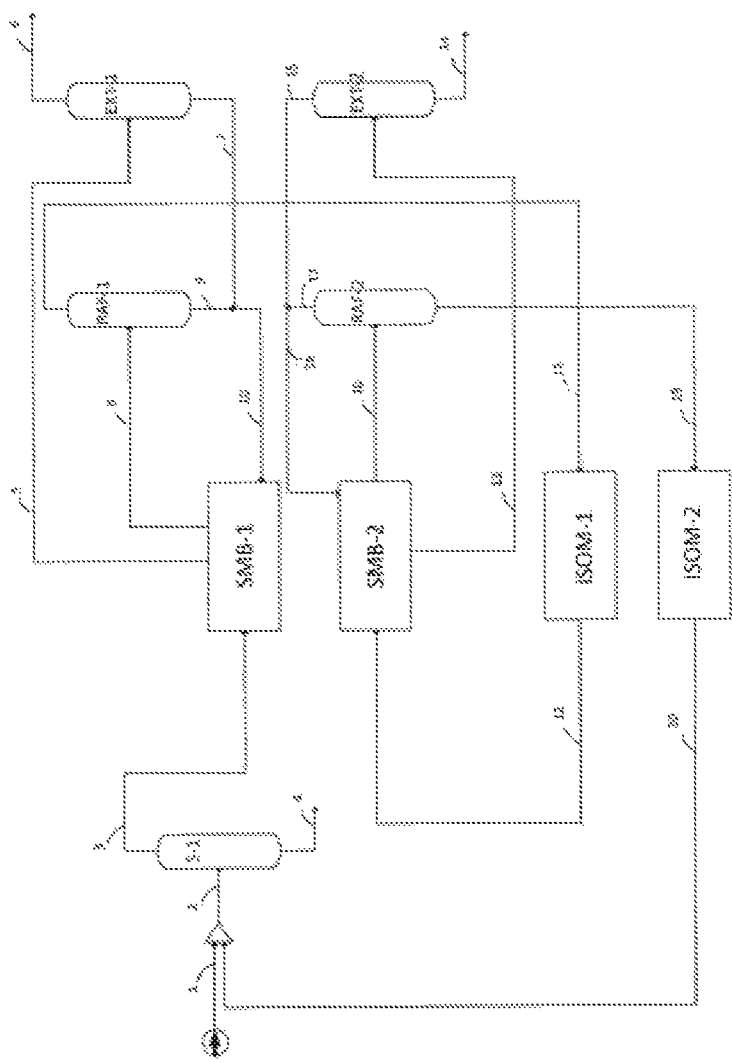
FIG. 2 shows a variant of the process according to the invention in which the separation unit (SMB-1) uses PDEB as desorbent and the separation unit (SMB-2) uses toluene as adsorbant. The toluene is therefore recovered at the top of the distillation columns (EXT-2) and (RAF-2), as toluene is lighter than the C8 aromatics.

FIG. 2 represents a variant of the layout of the process according to the invention that differs from that of FIG. 1 in that the separation unit (SMB-1) uses PDEB as desorbent and toluene as desorbent of the separation unit (SMB-2).

Unlike the separation unit (SMB-1) using PDEB, the separation unit (SMB-2) recovers the desorbent (toluene) at the top of the column EXT-2 and RAF-2, as the toluene is lighter than the C8-aromatics.

The fact of using two different desorbents in the two separation units (SMB-1 and SMB-2) has the advantage of avoiding the accumulation of aromatic impurities such as benzene and the heavy C9 and C10 aromatic compounds.

Using two different desorbents in the two separation units (SMB-1 and SMB-2) also makes it possible to carry out a thermal integration between the columns (EXT-1) and (EXT-2) and (RAF-1) and (RAF-2). In fact, the top of the distillation column (EXT-1) can potentially reboil all or part of the distillation column (EXT-2) and the top of the column (RAF-1) can potentially reboil all or part of the distillation column (RAF-2)

EXAMPLES ACCORDING TO THE INVENTION

Figure 3:
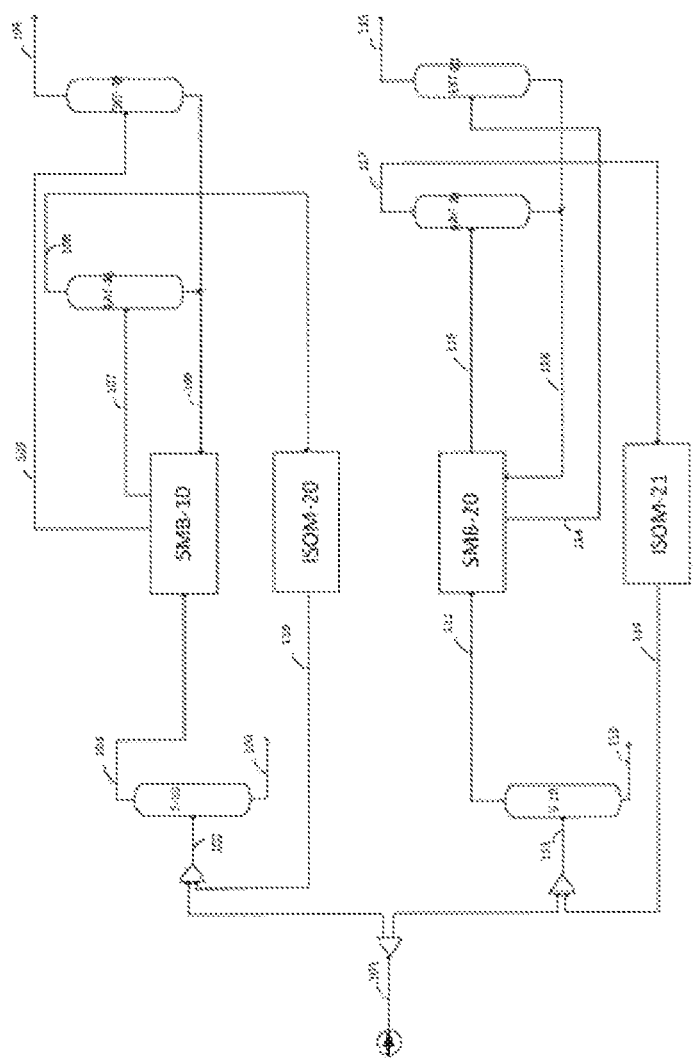
FIG. 3 shows a layout of the process according to the prior art and serves to illustrate Example 1 which is according to the prior art.

Example 1 According to the Prior Art (FIG. 3)

This example illustrates the prior art and describes an aromatic complex constituted by two C8-aromatic loops in parallel, which are typical of the industrial complexes in which the quantity of paraxylene produced is greater than the capacity that can be accepted by a single C8-aromatic loop, as shown in FIG. 3 and comprising:
two xylenes columns (S-10 and S-20) making it possible to extract the C9 and C10 aromatics (flow 104 and 113) and to send a flow (103) and a flow (112) essentially constituted by C8 aromatics to the separation units (SMB-10 and SMB-20),
a first simulated moving bed separation unit (SMB-10) with 4 zones from which an extract (105) and a single raffinate (107) are drawn off,
a first isomerization unit (ISOM-10) supplied with a part (108) of the raffinate (107) after elimination of the desorbent (109) by means of the distillation column (RAF-10),
a first paraxylene extraction column (EXT-10) from which the desorbent which is recycled to the separation unit (SMB-1) via the flow (109) is drawn off at the bottom and a cut rich in paraxylene (106) is drawn off at the top,
a second simulated moving bed separation unit (SMB-20) with 4 zones from which an extract (114) and a single raffinate (116) are drawn off,
a second isomerization unit (ISOM-20) supplied with a part (117) of the raffinate (116) after elimination of the desorbent (118) by means of the distillation column (RAF-20),
a second paraxylene extraction column (EXT-20) from which the desorbent which is recycled to the adsorption unit (SMB-2) via the flow (118) is drawn off at the bottom and a cut rich in paraxylene (115) is drawn off at the top.

The material balance of the process is described in the table below. Only the C8-aromatic and C9+ compounds are described. The other compounds and the formation of C9+ in the isomerization units are disregarded. The unit used for the flow rate is kilotonne per year (kt/yr).

TABLE 1

|  |  | PX | EB | MOX | C9+ | Total |
|---|---|---|---|---|---|---|
| Fresh feedstock | 101 | 23.6 | 15.6 | 67.7 | 13.8 | 120.6 |
| S-10 feedstock | 102 | 50.0 | 22.9 | 148.5 | 6.9 | 228.3 |
| SMB-10 feedstock | 103 | 50.0 | 22.9 | 148.5 | 0 | 221.4 |
| S-10 bottom | 104 | 0 | 0 | 0 | 6.9 | 6.9 |
| EXT-10 top | 106 | 50.0 | 0 | 0 | 0 | 50.0 |
| ISOM-10 inlet | 108 | 0 | 22.9 | 148.5 | 0 | 171.4 |
| ISOM-10 outlet | 110 | 38.2 | 15.1 | 114.7 | 0 | 168.0 |
| S-20 feedstock | 111 | 50.0 | 22.9 | 148.5 | 6.9 | 228.3 |
| SMB-20 feedstock | 112 | 50.0 | 22.9 | 148.5 | 0 | 221.4 |
| S-20 bottom | 113 | 0 | 0 | 0 | 6.9 | 6.9 |
| EXT-20 top | 115 | 50.0 | 0 | 0 | 0 | 50.0 |
| ISOM-20 inlet | 117 | 0 | 22.9 | 148.5 | 0 | 171.4 |
| ISOM-20 outlet | 119 | 38.2 | 15.1 | 114.7 | 0 | 168.0 |

The feedstock (101) which supplies the aromatic loop (mixture of the heavy reformate and toluene-column bottoms) has a flow rate of 120.6 kt/yr. This feedstock is divided into two equal flows of 60.3 kt/yr.

168 kt/yr of isomerate (110) recycled from the isomerization unit (ISOM-10) is added to a first part of the feedstock (101) so as to isomerize the ethylbenzene.

The resulting flow (102) is distilled in the xylenes column (S-10).

6.9 kt/yr of a mixture of C9 and C10 aromatics (104) is drawn off at the bottom of the column (S-10) and 221.4 kt/yr of a C8 aromatics cut (103) is drawn off at the top, of which the paraxylene content is 22.6%, the ethylbenzene content is 10.3% and the orthoxylene and metaxylene content is 67.1%.

This cut is sent into a simulated moving bed separation unit with four zones (SMB-10) and four main flows: the feedstock (103), the desorbent (109), the extract (105) and the raffinate (107). This unit is composed of 12 beds containing an X zeolite exchanged with barium. The temperature is 175° C. The configuration is: 2 beds in zone 1, 5 beds in zone 2, 3 beds in zone 3 and 2 beds in zone 4. The solvent used is paradiethylbenzene.

The extract (105) at the outlet of the separation unit (SMB-10) is sent into a distillation column (EXT-10) from which the desorbent recycled to the separation unit (SMB-10) is drawn off at the bottom, and 50 kt/yr of a mixture (106), essentially constituted by toluene and paraxylene, is drawn off at the top.

The raffinate is sent into a distillation column (RAF-10) from which the desorbent recycled to the separation unit (SMB-10) is drawn off at the bottom, and 171.4 kt/yr of a mixture (108) is drawn off at the top.

This flow is sent into an isomerization unit (ISOM-10).

The isomerization unit (ISOM-10) operates in gas phase under the following conditions:
Temperature: 385° C.
Catalyst: contains 0.2 by weight of platinum and EU-1 zeolite
Hourly space velocity: 3.5 h$^{-1}$
H2/hydrocarbons ratio: 4.4:1
Pressure: 0.9 MPa The ethylbenzene content of the mixture introduced into the isomerization unit (ISOM-10) is 13.4%.

A 2% loss by cracking is observed in this isomerization, i.e. a flow rate of 3.4 kt/yr. The ethylbenzene is partially isomerized, 9% of it remains in the outlet flow (110).

This isomerate (110) has a flow rate of 168 kt/yr. It is recycled to the inlet of the column S-10 where it is mixed with a part of the fresh feedstock (101) which has a flow rate of 60.3 kt/yr.

168 kt/yr of isomerate (119) recycled from the isomerization unit (ISOM-20) is added to a first part of the feedstock (101) so as to isomerize the ethylbenzene. The resulting flow (111) is distilled in the xylenes column (S-20).

6.9 kt/yr of a mixture of C9 and C10 aromatics (flow 113) is drawn off at the bottom of the distillation column (S-20) and 221.4 kt/yr of a C8 aromatics cut (flow 112) is drawn off at the top, of which the paraxylene content is 22.6%, and the ethylbenzene content is 10.4%.

This cut is sent into a simulated moving bed adsorption unit with four zones (SMB-20) and four main flows: the feedstock (flow 112), the desorbent (flow 118), the extract (flow 114) and the raffinate (flow 116).

This unit is composed of 12 beds containing an X zeolite exchanged with barium.

The temperature is 175° C. The configuration is: 2 beds in zone 1, 5 beds in zone 2, 3 beds in zone 3 and 2 beds in zone 4. The solvent used is paradiethylbenzene.

The extract (114) at the outlet of the separation unit (SMB-20) is sent into a distillation column (EXT-20) from which the desorbent recycled to the adsorption unit (SMB-20) is drawn off at the bottom and 50 kt/yr of a mixture (115) essentially constituted by toluene and paraxylene is drawn off at the top.

The raffinate is sent into a distillation column (RAF-20) from which the desorbent recycled to the separation unit (SMB-20) is drawn off at the bottom, and 171.4 kt/yr of a mixture (117) is drawn off at the top.

This flow is sent into an isomerization unit (ISOM-20). The isomerate obtained (119) is recycled to the inlet of the distillation column S-20 where it is mixed with a part of the fresh feedstock (101).

The isomerization unit (ISOM-20) operates in gas phase under the following conditions:
Temperature: 385° C.
Catalyst: contains 0.2 by weight of platinum and EU-1 zeolite
Hourly space velocity: 3.5 h$^{-1}$
H2/hydrocarbons ratio: 4.4/1
Pressure: 0.9 MPa The ethylbenzene content of the mixture introduced into the isomerization unit (ISOM-20) is 13.4%.

A 2% loss by cracking is observed in this isomerization, i.e. a flow rate of 3.4 kt/yr. The ethylbenzene is partially isomerized, 9% of it remains in the outlet flow (119).

This isomerate (119) has a flow rate of 168 kt/yr; it is recycled to the inlet of the S-20 column where it is mixed with a part of the fresh feedstock (101) which has a flow rate of 60.3 kt/yr.

Example 2 According to the Invention

This example illustrates the invention and describes an aromatic loop shown in FIG. 1 and comprising:
- a xylenes column (S-1) making it possible to extract the C9 and C10 aromatics (4) and to send a flow (3) essentially constituted by C8 aromatics to the adsorption unit (SMB-1),
- a first simulated moving bed separation unit (SMB-1) with 4 zones from which an extract (5) and a raffinate (8) are drawn off,
- a first paraxylene extraction column (EXT-1) from which the desorbent (7) which is recycled to the separation unit (SMB-1) via the flow (10) is drawn off at the bottom and a cut rich in paraxylene (6) is drawn off at the top,
- a second simulated moving bed separation unit (SMB-2) with 4 zones from which an extract (13) and a raffinate (16) are drawn off,
- a second paraxylene extraction column (EXT-2) from which the desorbent (15) which is recycled to the separation unit (SMB-2) via the flow (18) is drawn off at the bottom and a cut rich in paraxylene (14) is drawn off at the top.
- a first isomerization unit (ISOM-1) supplied with the first raffinate (11) after elimination of the desorbent (9) by means of the distillation column (RAF-1),
- a second isomerization unit (ISOM-2) supplied with the second raffinate (19) after elimination of the desorbent (17) by means of the distillation column (RAF-2), The material balance of the process is described in Table 2 below. Only the C8- and C9+ compounds are described; the other compounds and the formation of C9+ in the isomerization units are disregarded. The unit used for the flow rate is kilotonne per year (kt/yr).

TABLE 2

|  |  | PX | EB | MOX | C9 | Total |
|---|---|---|---|---|---|---|
| Fresh feedstock | 1 | 22.7 | 15.3 | 65.1 | 13.3 | 116.4 |
| S-1 feedstock | 2 | 57.6 | 29.1 | 169.7 | 13.3 | 269.7 |
| SMB-1 feedstock | 3 | 57.6 | 29.1 | 169.7 | 0 | 256.4 |
| S-1 bottom | 4 | 0 | 0 | 0 | 13.3 | 13.3 |
| EXT-1 top | 6 | 57.6 | 0 | 0 | 0 | 57.6 |
| ISOM-1 feedstock | 11 | 0 | 29.1 | 169.7 | 0 | 198.8 |
| ISOM-1 outlet | 12 | 42.4 | 29.1 | 127.3 | 0 | 198.8 |
| EXT-2 top | 14 | 42.4 | 0 | 0 | 0 | 42.4 |
| ISOM-2 inlet | 19 | 0 | 29.1 | 127.3 | 0 | 156.4 |
| ISOM-2 outlet | 20 | 34.9 | 13.8 | 104.6 | 0 | 153.3 |

The fresh feedstock (1) which supplies the aromatic loop has a flow rate of 116.4 kt/yr. 153.3 kt/yr of isomerate (20) recycled from the isomerization unit (ISOM-2) is added to this feedstock, isomerizing the ethylbenzene. The resulting flow (2) is distilled in the xylenes column (S-1).

13.3 kt/yr of a mixture of C9 and C10 aromatics (4) is drawn off at the bottom of the distillation column (S-1) and 256.4 kt/yr of a cut of C8 aromatics (3) is drawn off at the top, of which the paraxylene content is approximately 22.5%, the ethylbenzene content is approximately 11.3%, and the orthoxylene and metaxylene content is approximately 66.2%.

This C8-aromatics cut is sent into a simulated moving bed separation unit with four zones (SMB-1) and four main flows: the feedstock (3), the desorbent (10), the extract (5) and the raffinate (8). This unit is composed of 12 beds containing an X zeolite exchanged with barium. The temperature is 175° C. The configuration is: 2 beds in zone 1, 5 beds in zone 2, 3 beds in zone 3 and 2 beds in zone 4.

The solvent used is paradiethylbenzene.

The extract (5) at the outlet of the separation unit (SMB-1) is sent into a distillation column (EXT-1) from which the desorbent (7) recycled to the separation unit (SMB-1) is drawn off at the bottom, and 57.6 kt/yr of a mixture (6) essentially constituted by toluene and paraxylene is drawn off at the top.

The raffinate (8) is sent into a distillation column (RAF-1) from which the desorbent (9) recycled to the adsorption unit (SMB-1) is drawn off at the bottom, and 198.8 kt/yr of a mixture (11) is drawn off at the top.

This flow (11) is sent into an isomerization unit (ISOM-1).

The isomerization unit (ISOM-1) operates in liquid phase under the following conditions:
Temperature: 240° C.
Catalyst: contains ZSM-5 zeolite
Hourly space velocity: 3 h$^{-1}$
Pressure: 1.9 MPa The ethylbenzene content of the mixture introduced into the isomerization unit (ISOM-1) is approximately 14.6%.

As the ethylbenzene is not converted, the quantity thereof is therefore the same in the outlet flow (12).

This isomerate (12) has a flow rate of 198.8 kt/yr. It is recycled to the inlet of the adsorption unit (SMB-2) without passing through the column (S-1).

The isomerate (12) originating from the isomerization unit (ISOM-1) supplies a second simulated moving bed separation unit with four zones (SMB-2) and four main flows: the feedstock (12), the desorbent (18), the extract (13) and the raffinate (16).

This unit is composed of 12 beds containing an X zeolite exchanged with barium.

The temperature is 175° C. The configuration is: 2 beds in zone 1, 5 beds in zone 2, 3 beds in zone 3 and 2 beds in zone 4. The solvent used is paradiethylbenzene.

The extract (13) at the outlet of the separation unit (SMB-2) is sent into a distillation column (EXT-2) from which the desorbent (15) recycled to the separation unit (SMB-2) is drawn off at the bottom, and 42.4 kt/yr of a mixture (14) essentially constituted by toluene and paraxylene is drawn off at the top.

The raffinate (16) is sent into a distillation column (RAF-2) from which the desorbent (17) recycled to the separation unit (SMB-2) is drawn off at the bottom, and 156.4 kt/yr of a mixture (19) is drawn off at the top.

This flow (19) is sent into an isomerization unit (ISOM-2).

The isomerization unit (ISOM-2) operates in gas phase under the following conditions:
Temperature: 385° C.
Catalyst: contains 0.2% by weight of platinum and EU-1 zeolite
Hourly space velocity: 3.5 h$^{-1}$
Pressure: 0.9 MPa The ethylbenzene content of the mixture introduced into the isomerization unit (ISOM-2) is approximately 18.6%. A 2% loss by cracking is observed in this isomerization unit, i.e. a flow rate of 3.1 kt/yr.

The ethylbenzene is partially isomerized; 9% of it remains in the outlet flow (20).

The isomerate (20) has a flow rate of 153.3 kt/yr; it is recycled to the inlet of the column S-1 where it is mixed with the fresh feedstock (1) which has a flow rate of 116.4 kt/yr.

The invention has several advantages compared with the prior art.

Firstly, the liquid-phase isomerization unit consumes less energy than gas-phase isomerization.

In fact, it operates at a lower temperature. It also operates without hydrogen recycling, therefore without a recycling compressor.

Finally, the liquid-phase isomerization unit produces a much lower quantity of by-products, in particular of the C9 aromatics, which makes it possible to by-pass the C9 aromatics elimination column (S-1) greatly reducing the energy required for this separation. The fact of coupling a liquid-phase isomerization to a gas-phase isomerization isomerizing the ethylbenzene makes it possible to reduce the losses by cracking.

In fact in order to output 100 kt/yr of paraxylene, it is necessary to introduce 103.1 kt/yr of C8 aromatic compounds (calculated as the difference 116.4-13.3 kt/yr) into the fresh feedstock in the process according to the invention, as against 106.8 kt/yr of C8 aromatic compounds (calculated as the difference 120.6-13.8 kt/yr) for the process according to the prior art.

The invention claimed is:

1. A process for producing high-purity paraxylene based on a xylenes cut containing ethylbenzene and C9+ compounds, a which process is performed in an apparatus that contains two simulated moving bed separation units (SMB-1 and SMB-2), and two isomerization units (ISOM-1 and ISOM-2), wherein ISOM-1 operates in liquid phase and ISOM-2 operates in gas phase, said process consisting of the following series of stages:

sending a feedstock (2) comprising metaxylene, paraxylene, orthoxylene, ethylbenzene, and C9+ compounds to a distillation column (S-1) from where a mixture (3) is drawn off at a top comprising a major part of the metaxylene, paraxylene, and ethylbenzene, and at least a part of the orthoxylene, and a flow (4) of C9-C10 hydrocarbons and the remaining part of the orthoxylene is drawn off at a bottom, carrying out a first separation of the mixture from the top (3) in the separation unit (SMB-1) comprising at least one adsorber containing a plurality of interconnected beds and operating in a closed loop, said unit comprising at least four zones delimited by injections of the mixture (3) and a first desorbent (10), resulting from a mixture of flows (9) and (7), and draw-offs of a first extract (5) enriched with paraxylene and a first raffinate (8) depleted of paraxylene, carrying out a second separation of a first isomerate (12) originating from the isomerization unit (ISOM-1) in the separation unit (SMB-2), said separation unit (SMB-2) being constituted by at least one adsorber containing a plurality of interconnected beds and operating optionally in a closed loop, and said unit comprising at least four zones delimited by injections of the first isomerate (12) and of a second desorbent (18), resulting from a mixture of flows (17) and (15), and draw-offs of a second extract (13) enriched with paraxylene and a second raffinate (16) depleted of paraxylene, distilling the first extract (5) originating from the separation unit (SMB-1) in a distillation column (EXT-1) to recover a flow (6) enriched with paraxylene, and a flow (7) which is sent as desorbent (10) to the separation unit (SMB-1), distilling the second extract (13) originating from the separation unit (SMB-2) in a distillation column (EXT- 2) to recover a flow (14) enriched with paraxylene, and a flow (15) which is sent as desorbent (18) to the separation unit (SMB-2), distilling the raffinate (16) originating from the separation unit (SMB-2) in a distillation column (RAF-2) to produce a flow (19) which is supplied to the isomerization unit (ISOM-2), and a flow (17) which is sent as desorbent (18) to the separation unit (SMB-2)

distilling the raffinate (8) originating from the separation unit (SMB-1) in a distillation column (RAF-1) to produce a flow (11) which is supplied to the isomerization unit (ISOM-1), and a flow (9) which is sent as desorbent (10) to the separation unit (SMB-1)

supplying the isomerization unit (ISOM-1) with flow (11) to obtain the first isomerate (12), supplying the second isomerization unit (ISOM-2) with flow (19) to obtain a second isomerate (20), which is recycled to the inlet of the distillation column (S-1), said isomerization unit (ISOM-2) operating in gas phase and under the following conditions:

a temperature greater than 300° C.,
a pressure less than 4.0 MPa,
an hourly space velocity less than 10 $h^{-1}$,
a hydrogen to hydrocarbon molar ratio less than 10, and in the presence of a catalyst in said isomerization unit (ISOM-2) comprising at least one zeolite having channels the opening of which is defined by a ring with 10 to 12 oxygen atoms (denoted 10 MR or 12 MR), and at least one group VIII metal at a content between 0.1 and 0.3% by weight, inclusive.

2. The process for the production of high-purity paraxylene based on a xylenes cut containing ethylbenzene and C9+ compounds according to claim 1, in which the isomerization unit (ISOM-1) operates in liquid phase under the following conditions:

a temperature less than 300° C.,
a pressure less than 4 MPa,
an hourly space velocity less than 10 $h^{-1}$,
in the presence of a catalyst comprising at least one zeolite having channels the opening of which is defined by a ring with 10 or 12 oxygen atoms (denoted 10 MR or 12 MR).

3. The process for the production of high-purity paraxylene based on a xylenes cut containing ethylbenzene and C9+ compounds according to claim 1, in which the catalyst for the gas-phase isomerization unit (ISOM-2) contains a zeolite of EUO or MOR structure type and platinum.

4. The process for the production of high-purity paraxylene based on a xylenes cut containing ethylbenzene and C9+ compounds according to claim 1, in which the separation unit (SMB-1) contains PDEB as desorbent.

5. The process for the production of high-purity paraxylene based on a xylenes cut containing ethylbenzene and C9+ compounds according to claim 1, in which the separation unit (SMB-2) contains toluene as desorbent.

6. The process for the production of high-purity paraxylene based on a xylenes cut containing ethylbenzene and C9+ compounds according to claim 1, in which the separation units (SMB-1) and (SMB-2) each contain from 6 to 24 beds, distributed over one or more adsorbers, the number of beds being adjusted so that each bed optionally has a height between 0.70 m and 1.40 m.

7. The process for the production of high-purity paraxylene based on a xylenes cut containing ethylbenzene and C9+ compounds according to claim 1, in which the distribution of the quantity of solid adsorbent in the separation units (SMB-1) and (SMB-2) is as follows:

the quantity of solid adsorbent in a zone 1 is 17%±5%,
the quantity of solid adsorbent in a zone 2 is 42%±5%,
the quantity of solid adsorbent in a zone 3 is 25%±5%,
the quantity of solid adsorbent in a zone 4 is 17%±5%,
wherein the zones are as follows:

zone 1 is between the injection of the desorbent and the draw-off of the extract,
zone 2 is between the draw-off of the extract and the injection of the feedstock,
zone 3 is between the injection of the feedstock and the draw-off of the raffinate,
zone 4 is between the draw-off of the raffinate and the injection of the desorbent.

8. The process for the production of high-purity paraxylene based on a xylenes cut containing ethylbenzene and C9+ compounds according to claim 1, in which, for the separation unit (SMB-1), a ratio by volume of desorbent to feedstock is at least 1.7/1.

9. The process for the production of high-purity paraxylene based on a xylenes cut containing ethylbenzene and C9+ compounds according to claim 1, in which, for the separation unit (SMB-2), a ratio by volume of desorbent to feedstock is at least 1.7/1.

10. The process for the production of high-purity paraxylene from a xylenes cut containing ethylbenzene and C9+ compounds according to claim 1, which is a process based on debottlenecking of an existing separation unit, constituted by two adsorbers used in series, as follows:

the last bed of the first adsorber is connected to the first bed of the first adsorber via a line containing at least one recirculation pump, this first adsorber acting as a separation unit (SMB-1), and
the last bed of the second adsorber is connected to the first bed of the second adsorber via a line containing at least one recirculation pump, this second adsorber acting as a separation unit (SMB-2).

11. The process for the production of high-purity paraxylene based on a xylenes cut containing ethylbenzene and C9+ compounds according to claim 1, in which the configuration of the two separation units (SMB-1) and (SMB-2) has a fixed number of beds in each of the chromatographic zones of each of the two separation units (SMB-1 and SMB-2).

12. The process for the production of high-purity paraxylene based on a xylenes cut containing ethylbenzene and C9+ compounds according to claim 1, in which a fraction of the isomerate (12) is sent to the distillation column (S-1).

13. The process for the production of high-purity paraxylene based on a xylenes cut containing ethylbenzene and C9+ compounds according to claim 1, wherein said isomerization unit (ISOM-2) operates in gas phase and under the following conditions:

a temperature of 350° C. to 480° C.,
a pressure of 0.5 to 2.0 MPa,
an hourly space velocity of 0.5 $h^{-1}$ to 6 $h^{-1}$,
a hydrogen to hydrocarbon molar ratio of 3 to 6.

14. The process for the production of high-purity paraxylene based on a xylenes cut containing ethylbenzene and C9+ compounds according to claim 1, in which the isomerization unit (ISOM-1) operates in liquid phase under the following conditions:

a temperature of 200 to 260° C.,
a pressure of 2 to 3 MPa,
an hourly space velocity of 2 $h^{-1}$ to 4 $h^{-1}$,
in the presence of a catalyst comprising at least one zeolite having channels the opening of which is defined by a ring with 10 oxygen atoms (denoted 10 MR).

15. The process for the production of high-purity paraxylene based on a xylenes cut containing ethylbenzene and C9+ compounds according to claim 1, in which the catalyst for the gas-phase isomerization unit (ISOM-2) contains an EU-1 zeolite and platinum.

16. The process for the production of high-purity paraxylene based on a xylenes cut containing ethylbenzene and C9+ compounds according to claim 1, in which the separation units (SMB-1) and (SMB-2) each contain from 8 to 15 beds, distributed over one or more adsorbers, the number of beds being adjusted so that each bed has a height between 0.70 m and 1.40 m.

17. The process for the production of high-purity paraxylene based on a xylenes cut containing ethylbenzene and C9+ compounds according to claim 1, in which, for the separation unit (SMB-1), a ratio by volume of desorbent to feedstock is between 1.5/1 and 0.4/1, inclusive.

18. The process for the production of high-purity paraxylene based on a xylenes cut containing ethylbenzene and C9+ compounds according to claim 1, in which, for the separation unit (SMB-2), a ratio by volume of desorbent to feedstock is between 1.5/1 and 0.4/1, inclusive.

19. The process for the production of high-purity paraxylene based on a xylenes cut containing ethylbenzene and C9+ compounds according to claim 1, in which the isomerization unit (ISOM-1) operates in the presence of a zeolite of the ZSM-5 type.

20. The process for the production of high-purity paraxylene based on a xylenes cut containing ethylbenzene and C9+ compounds according to claim 1, wherein the plurality of interconnected beds in (SMB-2) operate in a closed loop.

* * * * *